US012805942B2

(12) United States Patent
Lee et al.

(10) Patent No.: US 12,805,942 B2
(45) Date of Patent: Nov. 24, 2026

(54) HYSTERESIS COMPENSATION CONTROL APPARATUS OF FLEXIBLE TUBE AND METHOD THEREOF

(71) Applicant: ROEN Surgical, Inc., Daejeon (KR)

(72) Inventors: Dong-Ho Lee, Daejeon (KR); Joon-Hwan Kim, Daejeon (KR); Jong-seok Won, Daejeon (KR); Dong-Soo Kwon, Daejeon (KR)

(73) Assignee: ROEN Surgical, Inc., Daejeon (KR)

( * ) Notice: Subject to any disclaimer, the term of this patent is extended or adjusted under 35 U.S.C. 154(b) by 518 days.

(21) Appl. No.: 17/968,064

(22) Filed: Oct. 18, 2022

(65) Prior Publication Data

US 2023/0124057 A1 Apr. 20, 2023

(30) Foreign Application Priority Data

Oct. 18, 2021 (KR) ........................ 10-2021-0138056
Oct. 7, 2022 (KR) ........................ 10-2022-0128324

(51) Int. Cl.
*A61B 34/20* (2016.01)
*A61B 1/00* (2006.01)
(Continued)

(52) U.S. Cl.
CPC ........ *A61B 34/20* (2016.02); *A61B 17/00234* (2013.01); *G06N 20/00* (2019.01);
(Continued)

(58) Field of Classification Search
None
See application file for complete search history.

(56) References Cited

U.S. PATENT DOCUMENTS

2004/0138530 A1* 7/2004 Kawai .................... A61B 1/009 600/152
2009/0088773 A1* 4/2009 Zhao ...................... A61B 34/37 606/130
(Continued)

FOREIGN PATENT DOCUMENTS

CN 105943162 9/2016
JP H09188441 7/1997
(Continued)

OTHER PUBLICATIONS

U.S. Appl. No. 16/435,090, filed Sep. 26, 2019, Agrawal Varun, et al.

*Primary Examiner* — Shahdeep Mohammed
(74) *Attorney, Agent, or Firm* — JCIPRNET

(57) ABSTRACT

The present invention relates to a hysteresis compensation control apparatus of a flexible tube and a method thereof for compensation control of hysteresis of a surgical instrument disposed in a channel of an overtube. The hysteresis compensation control apparatus includes: an input unit receiving image information and tension information of a flexible surgical instrument required for mode switching; a mode switching determining unit for determining a current state of the surgical instrument on the basis of the image information of the surgical instrument, and generating a control mode switching signal according to the current state of the surgical instrument; a mode switching unit for switching a control mode from a flexible tube control based on the image information to a flexible tube control based on the tension information according to the control mode switching signal; and a compensation control unit for compensatingly controlling a flexible surgical instrument having hysteresis characteristics on the basis of a tension error value calculated by a learning model.

7 Claims, 9 Drawing Sheets

(51) Int. Cl.

| | |
|---|---|
| ***A61B 17/00*** | (2006.01) |
| ***A61M 25/01*** | (2006.01) |
| ***G06N 20/00*** | (2019.01) |
| ***G06T 7/00*** | (2017.01) |
| ***G06V 10/74*** | (2022.01) |
| ***G16H 40/63*** | (2018.01) |

(52) U.S. Cl.

CPC ............ *G06T 7/0012* (2013.01); *G06V 10/74* (2022.01); *G16H 40/63* (2018.01); *A61B 1/00154* (2013.01); *A61B 2017/00323* (2013.01); *A61B 2017/00694* (2013.01); *A61B 2034/2065* (2016.02); *A61M 2025/0166* (2013.01); *G06T 2207/20081* (2013.01); *G06T 2207/30004* (2013.01)

(56) References Cited

U.S. PATENT DOCUMENTS

| | | | | |
|---|---|---|---|---|
| 2020/0184248 | A1* | 6/2020 | Donhowe .............. | A61B 34/25 |
| 2020/0352554 | A1* | 11/2020 | Tully ..................... | A61B 34/74 |
| 2023/0329807 | A1* | 10/2023 | Heye ...................... | A61B 34/37 |

FOREIGN PATENT DOCUMENTS

| | | | |
|---|---|---|---|
| KR | 20200023640 | | 3/2020 |
| KR | 102340169 | B1 | 12/2021 |
| WO | 2015129802 | | 9/2015 |
| WO | 2021145490 | | 7/2021 |
| WO | 2021173315 | | 9/2021 |

* cited by examiner

HYSTERESIS COMPENSATION CONTROL APPARATUS OF FLEXIBLE TUBE AND METHOD THEREOF

BACKGROUND OF THE INVENTION

Field of the Invention

The present invention relates to a hysteresis compensation control apparatus of a flexible tube and a method thereof, and more specifically, to a hysteresis compensation control apparatus of a flexible tube and a method thereof for compensation control of hysteresis of a surgical instrument disposed in a channel of an overtube.

Background Art

As illustrated in FIG. 1, a flexible overtube 10 includes a plurality of flexible surgical instruments 21 and 22. The plurality of flexible surgical instruments 21 and 22 are inserted into channels 11 and 12 provided in a body of the overtube 10. As an example, the first surgical instrument 21 is towed by first and second traction wires (not shown) to control position and orientation.

The flexible surgical instrument has a hysteresis section as illustrated in FIG. 2. That is, even if the same traction power is given, the hysteresis section is generated according to the shape of the flexible overtube or the surgical instrument. There is a disadvantage in that the overtube or the surgical instrument cannot be precisely controlled in the hysteresis generation section.

PATENT LITERATURE

Patent Documents

US 2019/0290109

SUMMARY OF THE INVENTION

Accordingly, the present invention has been made to solve the above-mentioned problems occurring in the prior arts, and it is an object of the present invention to provide a hysteresis compensation control apparatus of a flexible tube and a method thereof capable of precisely controlling a flexible surgical instrument even in a hysteresis section.

The aspects of the present invention are not limited to those mentioned above, and other aspects not mentioned herein will be clearly understood by those skilled in the art from the following description.

To accomplish the above object, according to the present invention, there is provided a hysteresis compensation control apparatus of a flexible tube including: an input unit receiving image information and tension information of a flexible surgical instrument required for mode switching; a mode switching determining unit for determining a current state of the surgical instrument on the basis of the image information of the surgical instrument, and generating a control mode switching signal according to the current state of the surgical instrument; a mode switching unit for switching a control mode from a flexible tube control based on the image information to a flexible tube control based on the tension information according to the control mode switching signal; and a compensation control unit for compensatingly controlling a flexible surgical instrument having hysteresis characteristics on the basis of a tension error value calculated by a learning model.

Moreover, the image information for determining a current state of the surgical instrument is image information obtained by capturing a tip region of the surgical instrument inserted into a channel of a tube body and towed by a traction wire.

Furthermore, the input unit includes: a surgical instrument image capturing unit inserted into the channel of the tube body to capture an image of the surgical instrument; and a tension measuring unit for measuring traction force of a traction wire of the surgical instrument, wherein the image information of the tip region of the surgical instrument captured by the surgical instrument image capturing unit is transmitted to the mode switching determining unit to determine the current state of the surgical instrument.

Additionally, in the mode switching determining unit determines whether it is possible to control the image information-based flexible tube control mode on the basis of the image information of the tip region of the surgical instrument.

In addition, the hysteresis compensation control apparatus further includes: an image information learning unit for learning according to a predetermined learning model based on image information of the surgical instrument, and calculating an image error value by learning; and a tension information learning unit for learning according to a predetermined learning model based on the tension information of the surgical instrument, and calculating a tension error value by learning.

In another aspect of the present invention, there is provided a hysteresis compensation control apparatus including: a mode switching determining unit for generating a first control mode switching signal by determining a current state of a flexible surgical instrument on the basis of image information of the flexible surgical instrument or generating a second control mode switching signal by determining whether the control mode corresponds to a predefined tension control modeling on the basis of tension information of the flexible surgical instrument; an image mode switching unit for switching a control mode from a flexible tube control based on the tension information to a flexible tube control based on the image information; and a compensation control unit for compensatingly controlling the flexible surgical instrument having hysteresis characteristics by using a compensation error value generated on the basis of the tension information or the image information.

Moreover, the first control mode switching signal is generated when the tip region of the surgical instrument included in the image information determining the current state of the surgical instrument is not visible or is hidden by another surgical instrument.

Furthermore, the tension mode switching unit switches the control mode according to the first control mode switching signal.

Additionally, the second control mode switching signal is generated when there is no change in the load of the surgical instrument or when any one among the plurality of tension measurement values of the surgical instrument is zero and does not correspond to the tension control modeling.

In addition, the image mode switching unit switches the control mode according to the second control mode switching signal.

In a further aspect of the present invention, there is provided a hysteresis compensation control method including the steps of: compensatingly controlling a flexible surgical instrument having hysteresis characteristics on the basis of image information of a flexible surgical instrument; determining whether the surgical instrument is visible or not on the basis of image information for determining a current state of the surgical instrument; switching a control mode from an image information-based compensation control to a tension information-based compensation control when it is determined that the surgical instrument is not visible; and compensatingly controlling the flexible surgical instrument having the hysteresis characteristics on the basis of the tension information of the flexible surgical instrument.

Additionally, after the control mode is switched from the image information-based compensation control to the tension information-based compensation control, the hysteresis compensation control method further includes the steps of: determining whether the control mode corresponds to the predefined tension control modeling based on the tension information of the flexible surgical instrument; switching the control mode from the tension information-based compensation control to the image information-based compensation control when it is determined that the control mode does not correspond to the predefined tension control modeling; and compensatingly controlling the flexible surgical instrument having hysteresis characteristics on the basis of the image information of the flexible surgical instrument.

According to the present invention as described above, the hysteresis compensation control apparatus of a flexible tube and the method thereof can precisely control the flexible surgical instrument even in a hysteresis section.

BRIEF DESCRIPTION OF THE DRAWINGS

The above and other objects, features and advantages of the present invention will be apparent from the following detailed description of the preferred embodiments of the invention in conjunction with the accompanying drawings, in which.

DETAILED DESCRIPTION OF THE PREFERRED EMBODIMENT

Hereinafter, a preferred embodiment of the present invention will be described with reference to the drawings. In addition, the preferred embodiment described below does not limit the contents of the present invention as set forth in the claims, and the entire configuration described in this embodiment is not essential to the present invention as a solution of the present invention. Furthermore, it will be appreciated by those skilled in the art that the prior art and the obvious matters to those skilled in the art will be omitted, and descriptions of such omitted elements (methods) and functions could be sufficiently referred to within the scope of the present invention without departing from the spirit and scope of the present invention.

A hysteresis compensation control apparatus of a flexible tube according to an embodiment of the present invention is a device for compensatingly controlling hysteresis generated in a flexible tube. In this instance, the flexible tube is a tube driven or towed by a wire, and is, for instance, a flexible overtube or a flexible surgical instrument or a flexible robot surgical instrument inserted into a channel of the flexible overtube. Hereinafter, a flexible tube 10 or flexible surgical instruments 21 and 22 will be described as an example of the flexible tube.

For the flexible overtube 10, the flexible surgical instrument is inserted into a flexible tube body and the channel of the flexible tube. The flexible overtube 10 is an apparatus which is inserted into a human body, and controls the position and orientation of the flexible tube and the surgical instrument through a traction wire to operate the human body.

Figure 1:
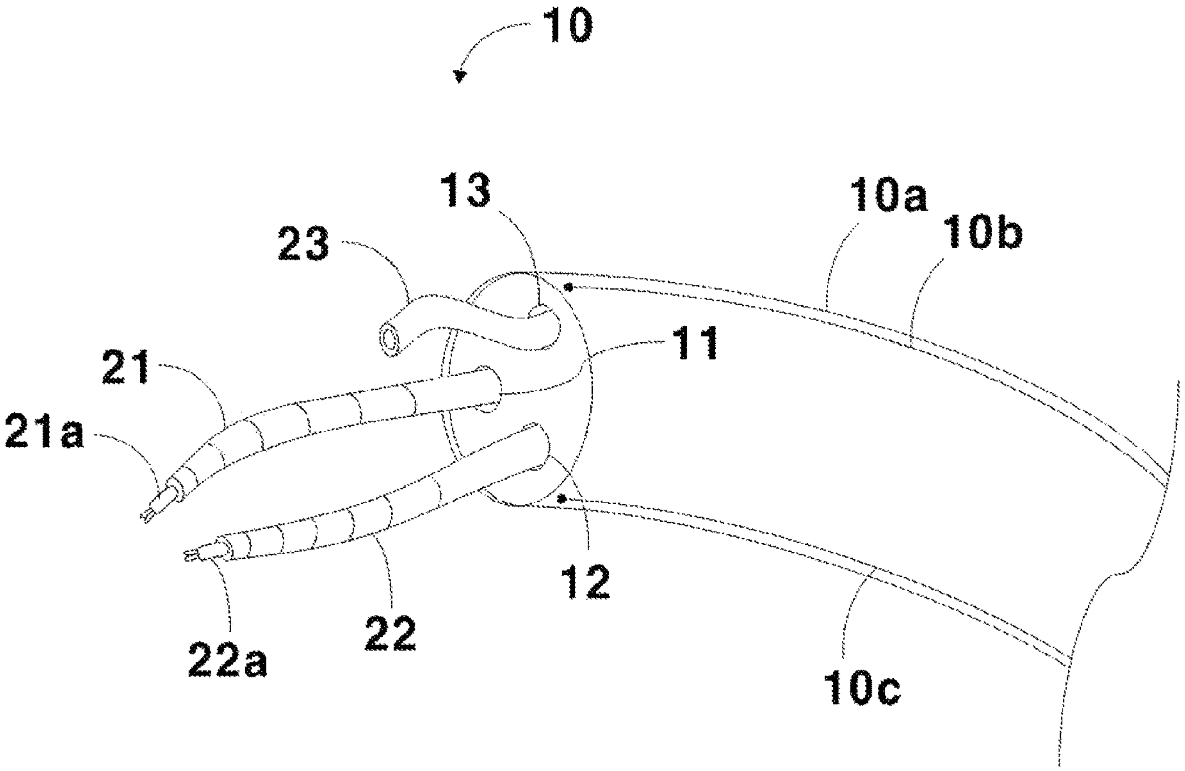
FIG. 1 is a diagram illustrating a flexible overtube according to an embodiment of the present invention.

As illustrated in FIG. 1, the flexible overtube or tube 10 includes an overtube body 10*a* having a flexible body, first, second, and third channels 11, 12 and 13 formed inside the overtube body 10*a* to have a predetermined diameter, and a surgical instrument and a camera unit inserted into each channel. As illustrated in FIG. 1, a first surgical instrument 21 is inserted into the first channel 11, a second surgical instrument 22 is inserted into the second channel 12, and the camera unit 23 is inserted into the third channel 13. However, the number of channels and the number of surgical instruments can be changed as needed. The camera unit 23 and the surgical instrument inserted into each channel protrude from the front end of the overtube body 10*a*. Accordingly, the camera unit 23 can capture the front side, and the surgical instruments can control the surgical operation for picking up or cut a tissue according to manipulation of the traction wire or a driving wire. A manipulation unit or a control unit (not shown) capable of manipulating the traction wire (not shown) is arranged at the rear end portion of the overtube body 10*a*. The traction wire is connected from the manipulation unit to the front end of the overtube body or the surgical instrument. Therefore, the position and orientation of the traction wire can be controlled by a user's manipulation. In this instance, as an example, in order to control the position and orientation of the flexible overtube body 10*a*, a first traction wire 10*b* and a second traction wire 10*c* are adjusted by a manipulation unit so that the position and orientation are changed according to the traction force. In addition, control in the position and orientation of each surgical instrument can be achieved in the same principle as the control in the position and orientation of the flexible overtube body 10*a*.

Figure 2:
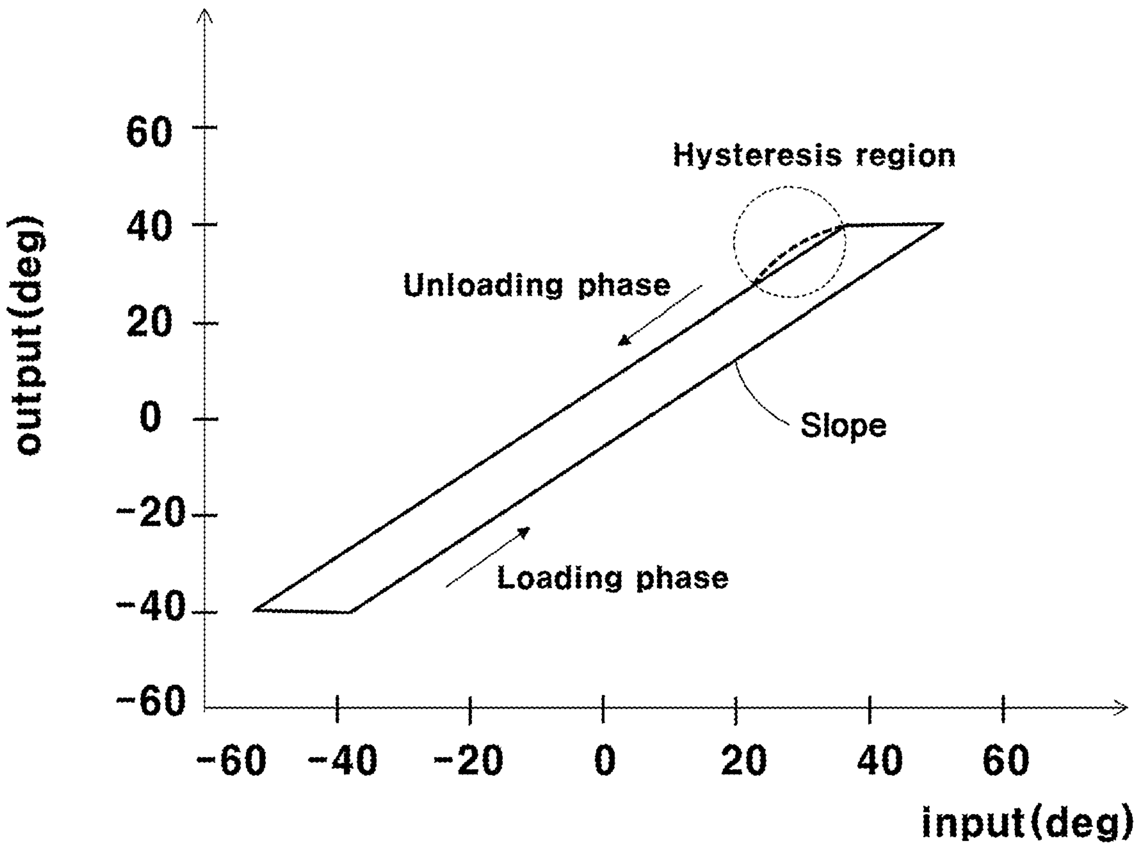
FIG. 2 is a graph showing hysteresis characteristics or curves of a flexible surgical instrument according to an embodiment of the present invention.

Meanwhile, as illustrated in FIG. 2, the flexible overtube body 10*a* or the flexible surgical instruments 21 and 22 have a linear slope section according to the traction force of the traction wire to control the position and orientation of the surgical instrument. However, as illustrated in FIG. 2, even though the same traction force is provided when the surgical instrument is controlled by using the traction wire, there is a section in which the position and orientation are not uniformly controlled to correspond to the traction force. Such a section is referred to as a hysteresis region. In such a hysteresis region, even though the traction force is the same, the position and orientation control of the surgical instrument may be varied. The reason why such hysteresis occurs is as follows. When the flexible surgical instrument or the flexible overtube is inserted into the body, the shape or twisting of the flexible surgical instrument or the flexible overtube is changed, and it causes generation of friction force between a wire and a wires sheath or cause a wire elongation due to the use of the traction wire. Moreover, even if a control command is input to tow the wire due to a slack of the wire, a dead zone where there is no change in output may be formed. Furthermore, ununiform tube characteristics may be generated due to the sheath or wire in the flexible overtube.

Therefore, the present invention can compensatingly control the flexible surgical instrument having such hysteresis characteristics, thereby precisely controlling the surgical instrument.

(Configuration and Function of Hysteresis Compensation Control Apparatus: First Embodiment)

Figure 3:
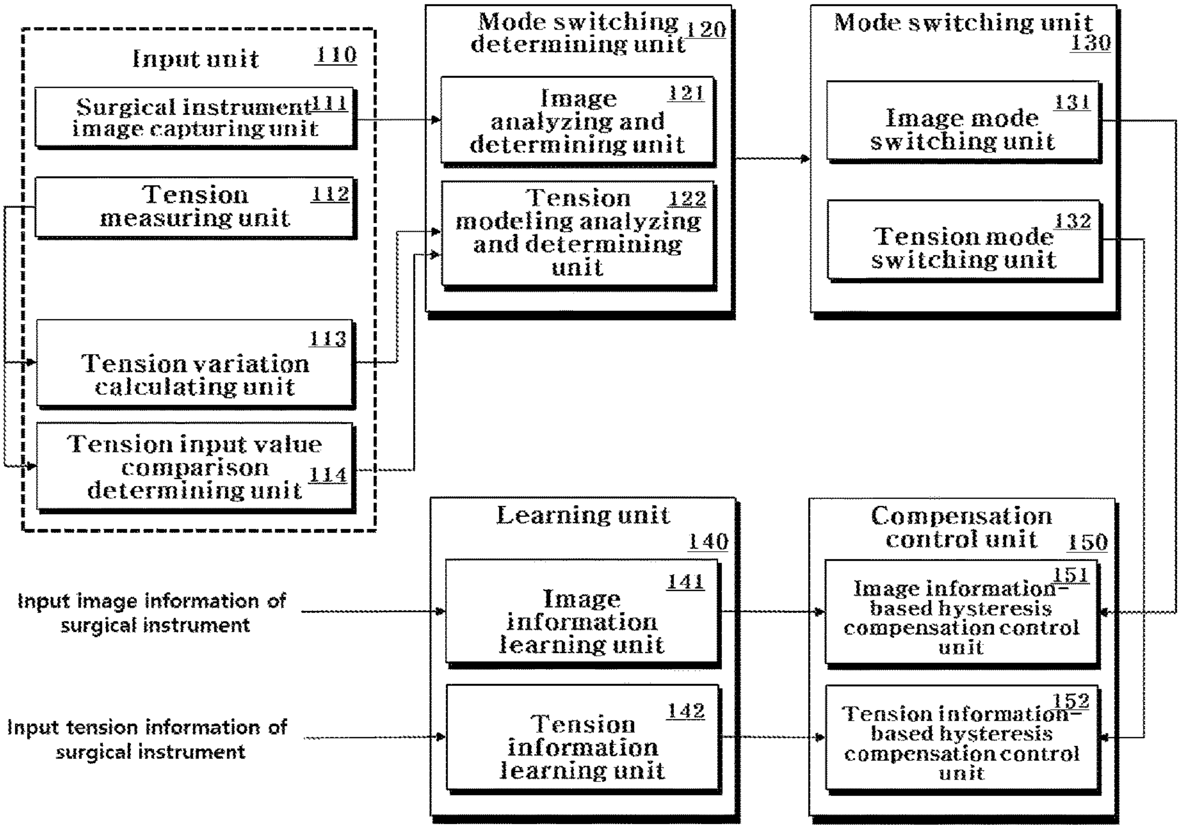
FIG. 3 is a schematic diagram of a hysteresis compensation control apparatus of a flexible overtube according to a first embodiment of the present invention.

As illustrated in FIG. 3, the hysteresis compensation control apparatus of the flexible overtube according to a first embodiment of the present invention includes an input unit 110, a mode switching determining unit 120, a mode switching unit 130, a learning unit 140, and a compensation control unit 150.

The input unit 110 receives image information and tension information of a flexible surgical instrument required for a mode switching for a hysteresis control. Accordingly, the input unit 110 includes a surgical instrument image capturing unit 111, a tension measuring unit 112, a tension variation calculating unit 113, and a tension input value comparison determining unit 114.

The surgical instrument image capturing unit 111 is inserted into the third channel 13, and then, is inserted into the first channel 11 so as to generate an image obtained by capturing an end effector of the first surgical instrument 21 or a tip 21*a* of the surgical instrument, which is an object for hysteresis compensation control. In this instance, in a case in which the control object is the second surgical instrument 22, the surgical instrument image capturing unit 111 may capture the second surgical instrument 22, and if necessary, may capture both the first and second surgical instruments 21 and 22. On the other hand, the surgical instrument image capturing unit 111 may be fixed, or if necessary, may be inserted and fixed into the channel in a movement-controllable structure. In this instance, it is preferable that the capturing conditions of the camera inserted into the actual body for surgical operation exactly correspond to the capturing position, the capturing angle, or the capturing region of the surgical instrument which has been already utilized in the learning unit 140 for learning.

The tension measuring unit 112 measures the traction force of the traction wire of the surgical instrument. In order to measure the traction force, for instance, a tension measuring sensor for measuring the tension of the traction wire is disposed, or a load of a motor driving the traction wire disposed in the manipulation unit is measured.

Figure 5:
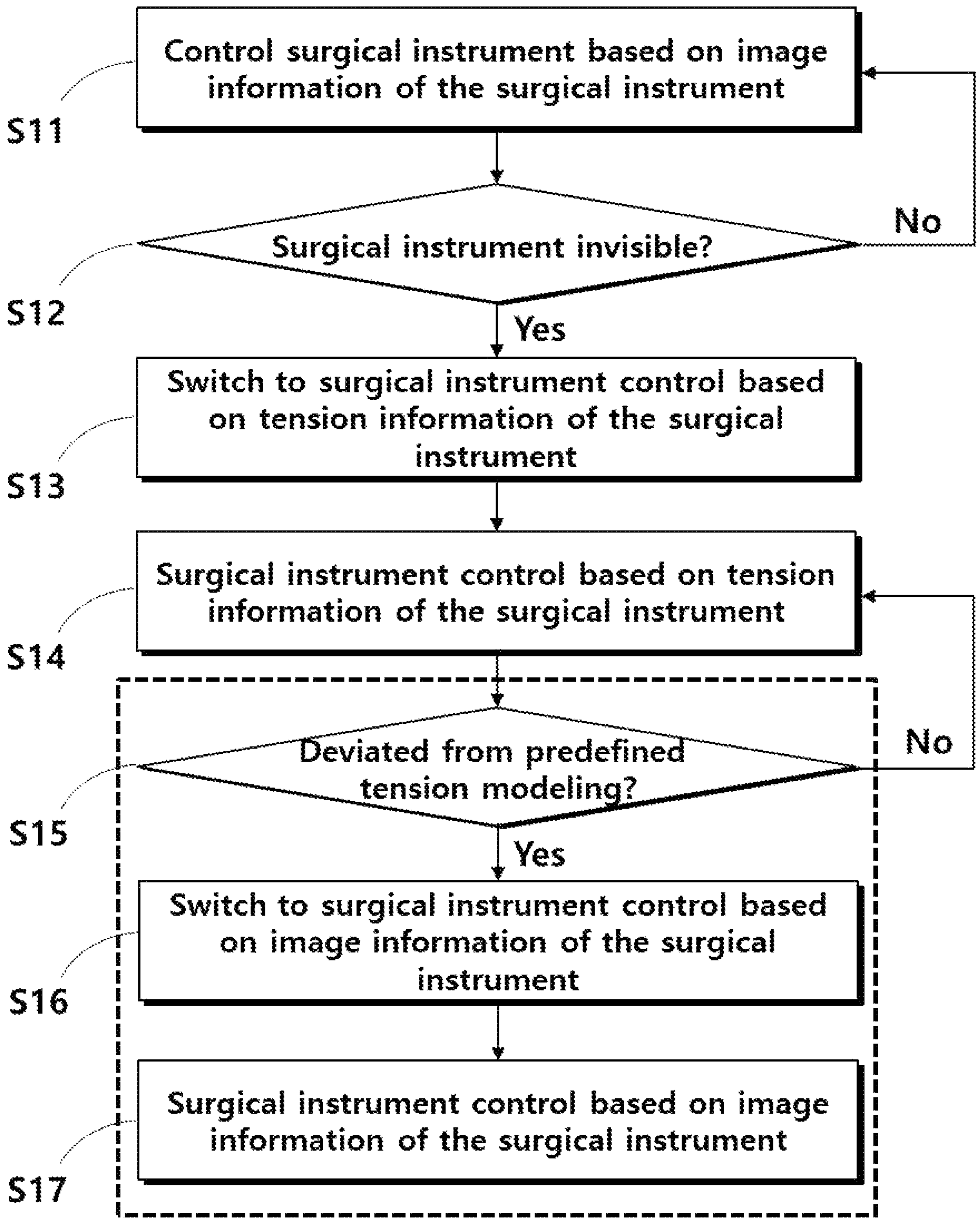
FIG. 5 is a graph illustrating a process of switching the control mode from the tension information-based hysteresis compensation control to the image information-based hysteresis compensation control in sequential order according to the first embodiment of the present invention after switching the control mode from the image information-based hysteresis compensation control to the tension information-based hysteresis compensation control.

As illustrated in FIG. 5, after the control mode is switched from a surgical instrument hysteresis compensation control based on image information to a surgical instrument hysteresis compensation control based on tension information, in order to switch the control mode to the surgical instrument hysteresis compensation control based on image information, the hysteresis compensation control apparatus further includes a tension variation calculating unit 113 and a tension input value comparison determining unit 114.

The tension variation calculating unit 113 calculates a variation of a wire tension value when a load is applied to the first surgical instrument 21, namely, the hysteresis compensation control object, which has no load, or when a load applied to the first surgical instrument 21 is disappeared. In order to control any one of the surgical instruments with the traction wire, the two traction wires as illustrated in FIG. 1 must be respectively manipulated. So, a measuring sensor for measuring wire tension or traction force of the first and second traction wires is required.

For convenience in description, one traction wire for each surgical instrument is described, but in fact, two traction wires are required to move one degree of freedom, and four traction wires are required to move two degrees of freedom. In addition, one driving motor per one traction wire is required or one driving motor per two traction wires is required.

The tension variation calculating unit 113 calculates a variation of the tension values measured by the measuring sensors. Through comparison of the variation of the tension values, it is found whether to change from no load to load or to change from load to no load. In the two cases, since the tension information-based hysteresis compensation control is difficult, the control mode must be switched. That is, in the above cases, the control mode must be switched from tension information-based control to image information-based control.

The tension input value comparison determining unit 114 finds which any one among tension measuring values or traction force measuring values of the first and second wires is ‘zero’. In a case in which any one among the tension values of the first and second wires is ‘zero’, since the tension information-based hysteresis compensation control is difficult, the control mode must be switched. That is, in the above cases, the control mode must be switched from tension information-based control to image information-based control. Hereinafter, assuming that the hysteresis compensation control object is the first surgical instrument 21, the present invention will be described. However, the hysteresis compensation control of the second surgical instrument 22 may be also described in the same principle.

The mode switching determining unit 120 according to an embodiment of the present invention determines the current state of the first surgical instrument 21 based on the image information of the first flexible surgical instrument 21 to generate a first control mode switching signal, which is a signal generated to switch the mode from the image information-based hysteresis compensation control to the tension information-based hysteresis compensation control.

The mode switching determining unit 120 determines whether the control mode corresponds a predefined tension control modeling on the basis of the tension information of the first surgical instrument 21 to generate a second control mode switching signal, which is a signal generated to switch the mode from the tension information-based hysteresis compensation control to the image information-based hysteresis compensation control.

The image information for determining the current state of the first surgical instrument 21 is image information obtained by capturing the tip 21*a* of the first surgical instrument 21.

The mode switching determining unit 120 includes an image analyzing and determining unit 121 and a tension modeling analyzing and determining unit 122.

The image analyzing and determining unit 121 receives an image of the tip area of the first surgical instrument 21 from the surgical instrument image capturing unit 111. The current state of the first surgical instrument 21 is determined through the received image. That is, in a case in which the tip area of the first surgical instrument 21 included in the image is not visible or the first surgical instrument 21 is hidden by the second surgical instrument 22, since the image information-based compensation control is impossible through the image analysis, the image analyzing and determining unit 121 generates a first control mode switching signal. The control mode is switched from the image information-based hysteresis compensation control to the tension information-based hysteresis compensation control according to the generated first control mode switching signal.

The tension modeling analyzing and determining unit 122 determines whether the control mode corresponds to the tension control modeling according to the input value of the tension variation calculating unit 113 or the tension input value comparison determining unit 114. When the tension modeling analyzing and determining unit 122 determines not to correspond to the tension control modeling, since the tension information-based compensation control is impossible any more, the tension modeling analyzing and determining unit 122 generates a second control mode switching signal. That is, the control mode is switched from the tension information-based hysteresis compensation control to the image information-based hysteresis compensation control. In this instance, for example, in a case in which a load of the first surgical instrument 21 is changed, namely, when a load is applied to the first surgical instrument 21, or when a load applied to the first surgical instrument 21 is disappeared, or in a case in which any one among the tension measuring values of the first and second traction wires towing the first surgical instrument 21 is 'zero', the cases do not correspond to the tension control modeling. The cases are not prediction models assumed for deep-learning of a tension information learning unit 142, which will be described later. In the above cases, the tension information-based hysteresis compensation control is impossible. Therefore, switching of the control mode is required.

The mode switching unit 130 according to an embodiment of the present invention includes an image mode switching unit 131 and a tension mode switching unit 132.

The image mode switching unit 131 switches the control mode from the image information-based compensation control of the first surgical instrument 21 to the tension information-based compensation control of the first surgical instrument 21 according to the first control mode switching signal of the image analyzing and determining unit 121.

The tension mode switching unit 132 switches the control mode from the image information-based compensation control of the first surgical instrument 21 to the tension information-based compensation control of the first surgical instrument 21 according to the second control mode switching signal of the tension modeling analyzing and determining unit 122.

The learning unit 140 according to an embodiment of the present invention performs deep learning or machine learning on the basis of image information or tension information, and calculates an image error value or a tension error value through learning. The learning unit 140 includes an image information learning unit 141 and a tension information learning unit 142.

The image information learning unit 141 performs machine learning or deep learning on the basis of the image of the tip 21*a* of the first surgical instrument 21. Therefore, it is preferable that the capturing conditions of the camera 23 for obtaining an image necessary for learning exactly correspond to the capturing conditions of the camera 23 when actually being inserted into a human body. The image information learning unit 141 calculates an image compensation control value or an image compensation error value corresponding to the image of the first surgical instrument 21 inserted into the body by learning according to a predefined learning model and captured now. The image compensation error value is transmitted to the compensation control unit 150. Of course, the generated image compensation error value may be information related to driving of the traction wire driving motor to actually drive the first surgical instrument.

The tension information learning unit 142 performs machine learning or deep learning based on the tension information of the traction wire of the first surgical instrument 21. The tension information learning unit 142 calculates a tension compensation control value or a tension compensation error value corresponding to the tension measuring value of the first surgical instrument 21 inserted into the body by learning according to the predefined learning model.

The compensation control unit 150 compensatingly controls the first surgical instrument 21 having a hysteresis curve by the image compensation error value or the tension compensation error value. The compensation control unit 150 includes an image information-based hysteresis compensation control unit 151 and a tension information-based hysteresis compensation control unit 152.

The image information-based hysteresis compensation control unit 151 performs a hysteresis compensation control of the first surgical instrument 21 using the image compensation error value. That is, the hysteresis compensation control is performed by the image information-based learning of the first surgical instrument captured currently.

The tension information-based hysteresis compensation control unit 152 performs a hysteresis compensation control of the first surgical instrument 21 using the tension compensation error value. That is, the hysteresis compensation control is performed by the tension information-based learning of the first surgical instrument captured currently.

(Hysteresis Compensation Control Method of Flexible Overtube)

Figure 4:
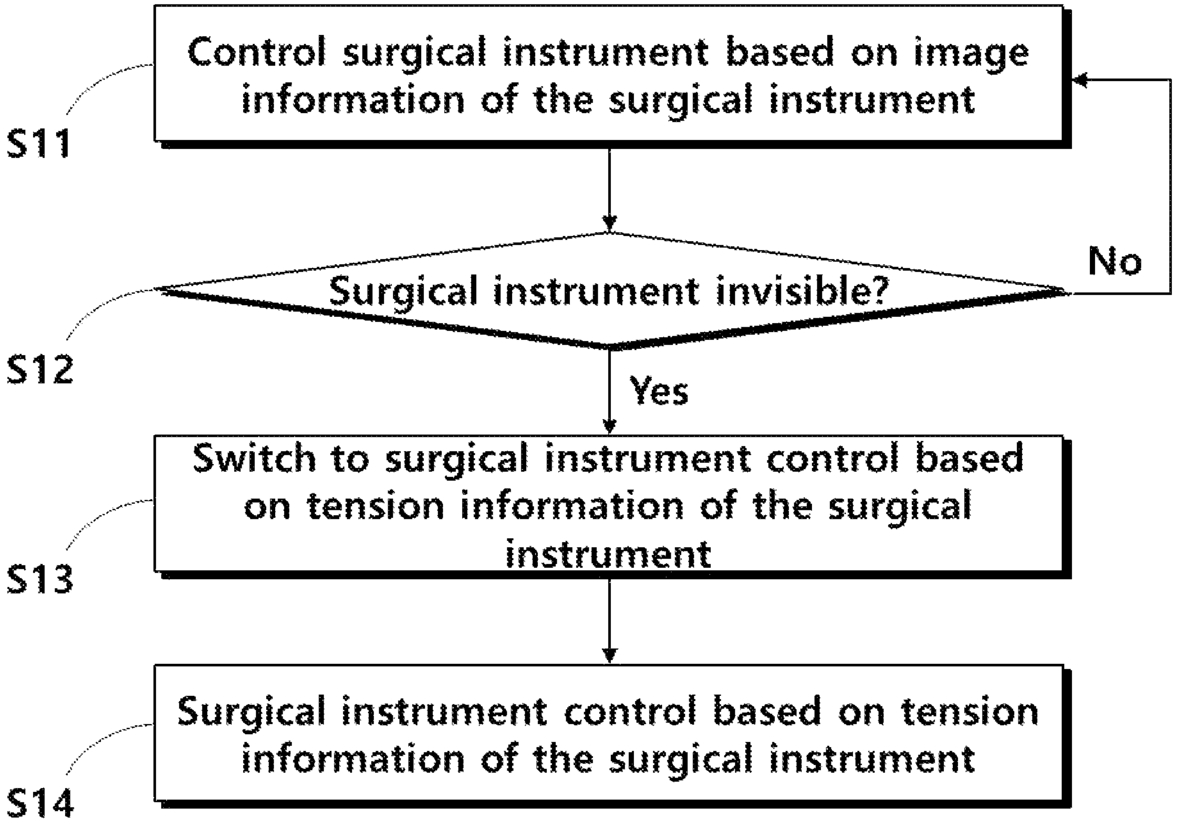
FIG. 4 is a view illustrating a process of switching a control mode from an image information-based hysteresis compensation control to a tension information-based hysteresis compensation control in sequential order according to the first embodiment of the present invention.

The hysteresis compensation control method of the flexible overtube according to an embodiment of the present invention includes a first method that the control mode is switched from the image information-based compensation control to the tension information-based compensation control as illustrated in FIG. 4, and a second method that the control mode is switched from the image information-based compensation control to the tension information-based compensation control and then is switched from the tension information-based compensation control to the image information-based compensation control. Hereinafter, the first method and the second method will be described.

As illustrated in FIG. 4, the method that the control mode is switched from the image information-based compensation control to the tension information-based compensation control is achieved through the following steps.

The compensation control unit 150 first compensatingly controls the first surgical instrument 21 having a hysteresis curve based on the image information of the first surgical instrument 21 (S11). More specifically, the image information-based hysteresis compensation control unit 151 controls tension of the traction wire of the first surgical instrument 21 based on the image information of the first surgical instrument 21.

In this instance, the image analyzing and determining unit 121 determines whether the first surgical instrument 21 is visible on the basis of the image information determining the current state of the first surgical instrument 21. In a case in which the first surgical instrument 21 is hidden or disappeared from a visible field of the camera unit 23, since the image information-based compensation control is impossible anymore, the image analyzing and determining unit 121 determines the current state of the first surgical instrument 21 (S12).

As a determination result, if it is determined that the surgical instrument is not visible, the mode switching unit 130 switches the control mode from the image information-based compensation control to the tension information-based compensation control (S13).

According to the switching of the control mode, the tension information-based hysteresis compensation control unit 152 compensatingly controls the first surgical instrument 21 having the hysteresis curve based on the tension information of the first surgical instrument 21.

Meanwhile, as illustrated in FIG. 5, after the control mode is switched from the image information-based compensation control to the tension information-based compensation control, the control mode is performed according to the following steps.

First, as illustrated in FIGS. 4 and 5, the steps from S11 to S14 are the same. The tension information-based hysteresis compensation control unit 152 compensatingly controls the first surgical instrument 21 based on the tension information of the first surgical instrument 21.

The tension modeling analyzing and determining unit 122 determines whether the control mode corresponds to the pre-defined tension control modeling based on the tension information of the first surgical instrument 21 after the control mode is switched from the image information-based compensation control to the tension information-based compensation control (S15). If the control mode does not correspond to the tension control modeling, the tension information-based compensation control cannot be performed anymore.

As a determination result, if it is determined that the control mode does not correspond to the predefined tension control modeling, the image mode switching unit 131 switches the control mode from the tension information-based compensation control to the image information-based compensation control (S16).

According to the switching of the control mode, the image information-based hysteresis compensation control unit 151 compensatingly controls the first surgical instrument 21 having the hysteresis curve based on the image information of the first surgical instrument 21.

(Configuration and Function of Hysteresis Compensation Control Apparatus: Second Embodiment)

Figure 6:
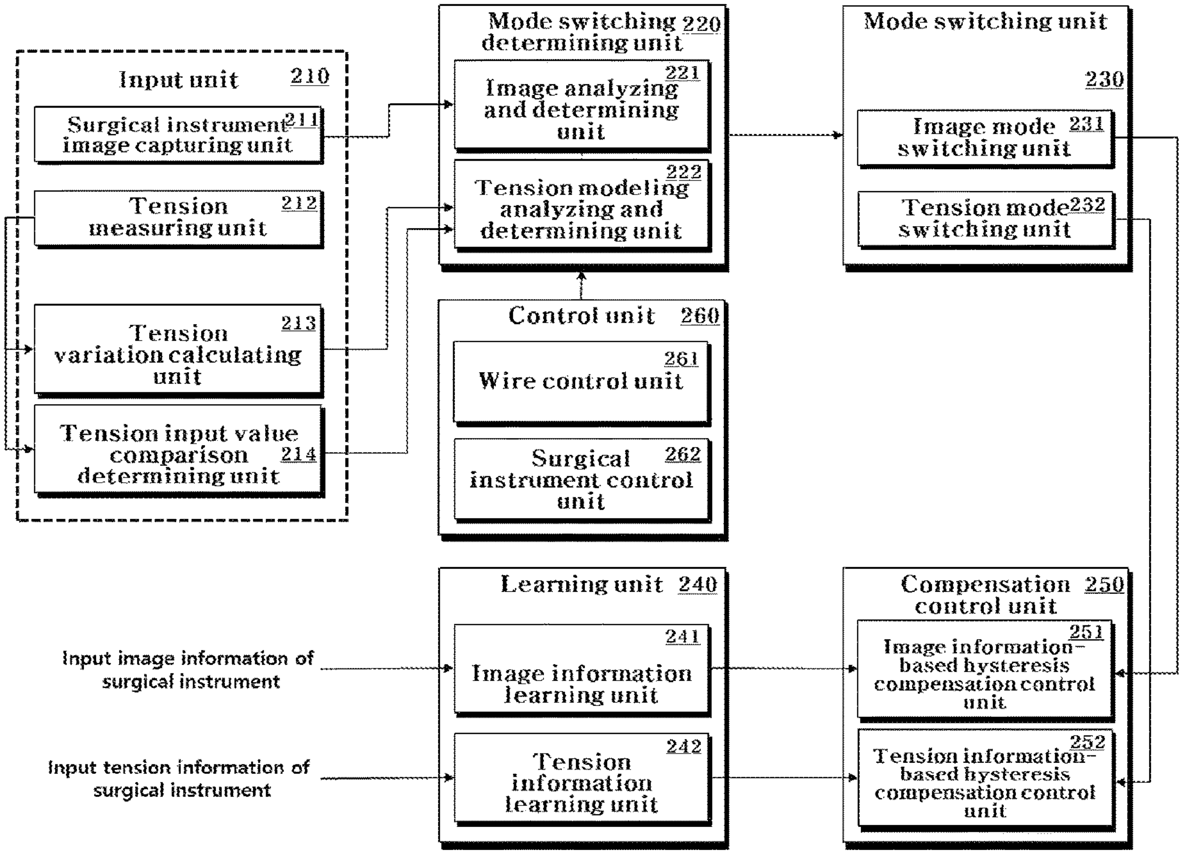
FIG. 6 is a schematic diagram of a hysteresis compensation control apparatus of a flexible overtube according to a second embodiment of the present invention.
Figure 7:
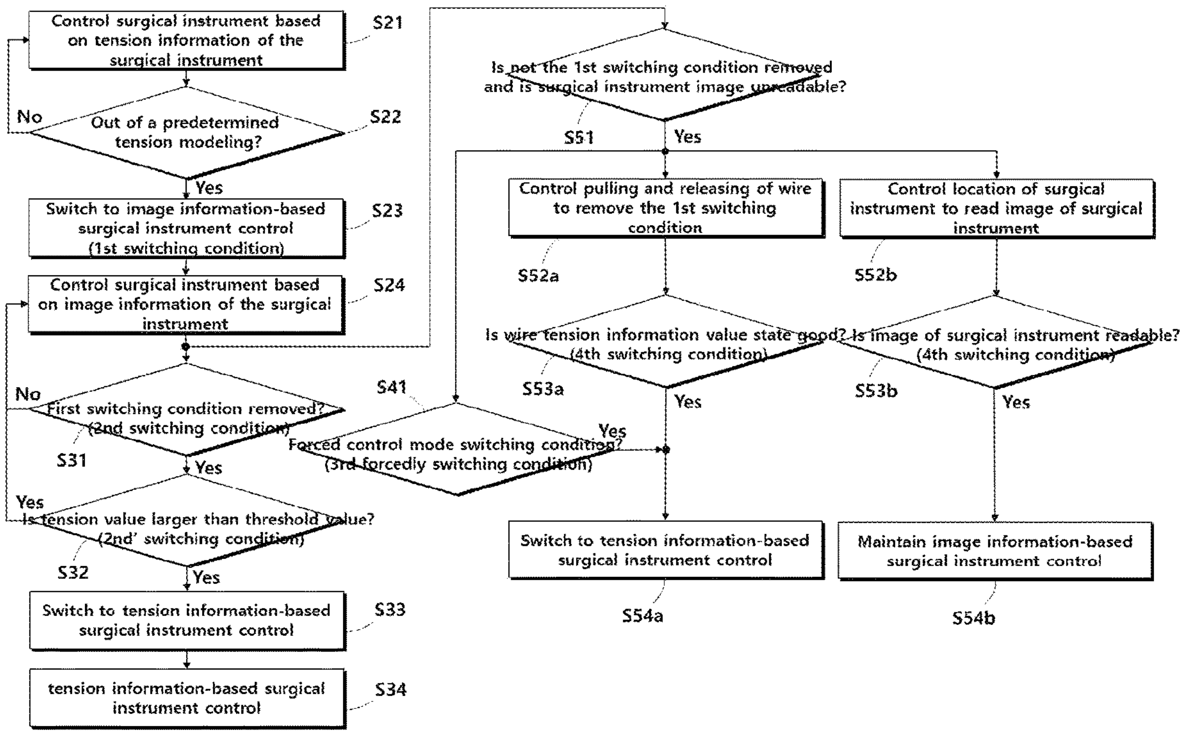
FIG. 7 is a graph illustrating a process of switching the control mode from an image information-based hysteresis compensation control to a tension information-based hysteresis compensation control in sequential order according to the second embodiment of the present invention after switching the control mode from a tension information-based hysteresis compensation control to an image information-based hysteresis compensation control.

Referring to FIGS. 6 and 7, a hysteresis compensation control apparatus of the flexible overtube according to a second embodiment of the present invention will be described in detail. The hysteresis compensation control apparatus of the flexible overtube according to the second embodiment of the present invention may refer to descriptions of the input unit 110, the mode switching determining unit 120, the mode switching unit 130, the learning unit 140, and the compensation control unit 150 of the first embodiment if necessary, and the same descriptions will be omitted.

As illustrated in FIG. 6, an input unit 210 receives image information and tension information of a flexible surgical instrument required for a mode switching. The input unit 210 includes a surgical instrument image capturing unit 211, a tension measuring unit 212, a tension variation calculating unit 213, and a tension input value comparison determining unit 214. Description of the input unit 110 substitutes for the description of the input unit 210. However, the tension input value comparison determining unit 214 receives tension measuring values of first and second wires, and finds which any one among the tension measuring values is ‘zero’. Accordingly, it is preferable to adjust traction force so that an initial tension measuring value according to the traction force of a wire is measured to be ‘zero’ or more even in no load.

A mode switching determining unit 220 includes an image analyzing and determining unit 221, and a tension modeling analyzing and determining unit 222. The mode switching determining unit 220 determines the current state of the surgical instrument based on the image information and the tension information of the flexible surgical instrument to generate control mode switching signals for switching control modes according to the current state of the surgical instrument. The control mode switching signals are respectively generated according to switching conditions. The mode switching determining unit 220 generates first and second switching condition control mode switching signals, a third forced switching condition control mode switching signal, and a signal for inducing a state change of the surgical instrument.

The tension modeling analyzing and determining unit 222 generates the first switching condition control mode switching signal, which switches the control mode from a tension information-based flexible tube control to an image information-based flexible tube control under the first switching condition determining that it is impossible to perform the tension information-based flexible tube control while performing a tension information-based control. The above description of the tension information-based control substitutes for an example of the first switching condition.

Furthermore, the tension modeling analyzing and determining unit 222 generates the second switching condition control mode switching signal, which switches the control mode from an image information-based flexible tube control into a tension information-based flexible tube control, under the second switching condition determining that it is impossible to perform the image information-based flexible tube control according to the signal of the image analyzing and determining unit 221 and determining that the first switching condition was removed, while performing the image information-based flexible tube control by the first switching condition control mode switching signal.

The image analyzing and determining unit 221 generates the third forced switching condition control mode switching signal which forcedly switches the control mode from the image information-based flexible tube control into the tension information-based flexible tube control, under the third forced switching condition determining that it is impossible to perform the image information-based flexible tube control and determining that the first switching condition was not removed, while performing the image information-based flexible tube control by the first switching condition control mode switching signal. As examples of the third forced switching condition, there are several cases in which a portion of at least one among the plurality of surgical instruments is not shown on an image, in which two or more surgical instruments are overlapped each other so that it is difficult to read the image due to an overlapped zone formed on the image, and in which it is difficult to read the image do to two or more surgical instruments getting in contact with each other. As other examples, there are several cases in which the visible field of the camera or the surgical instrument is blocked by the blood stained on a camera lens or the surgical instrument or by the organs in a human body or by smoke caused by resection of the bowel, in which it is difficult to grasp the surgical instrument since the entire image outline of the surgical instrument is changed by the organs or by the environment around the organs, and in which it is difficult to identify the image of the surgical instrument since LED illumination of the camera is reflected to the surgical instrument when any one among the surgical instruments hides the visible field of the camera.

The mode switching determining unit 220 generates the signal inducing a state change of the surgical instrument to make the tension information-based or the image information-based flexible tube control possible by controlling the wire or the surgical instrument, under the fourth switching condition determining that it is impossible to perform the image information-based flexible tube control and determining that the first switching condition was not removed, while performing the image information-based flexible tube control by the first switching condition control mode switching signal. The generated signal is transferred to a control unit 260 which will be described later.

The control unit 260 includes a wire control unit 261 and a surgical instrument control unit 262. The wire control unit 261 controls wires to control the tension information-based flexible tube by controlling the wires after receiving the signal inducing the state change of the surgical instrument from the mode switching determining unit 220. As an example, the control unit repeatedly controls the wire to be pulled or released so that a tension measurement value is measured if the wire is not broken.

Furthermore, the surgical instrument control unit 262 receives the signal inducing the state change of the surgical instrument from the mode switching determining unit 220 to control the surgical instrument image capturing unit 211 or the surgical instrument, so that it is possible to control the flexible tube based on the image-readable image information.

In a case in which the tension measurement value is input normally or is image-readable by the control of the control unit 260, the control unit generates a possible tension information signal and a possible image information signal, and transmits them to the mode switching determining unit 220.

The mode switching determining unit 220 generates a tension state change control mode switching signal, which switches the control mode from the image information-based flexible tube control into the tension information-based flexible tube control when the possible tension information signal is received from the control unit 260. The mode switching determining unit 220 is continuously controlled in the image information-based flexible tube control mode when receiving the possible image information signal from the control unit 260. Therefore, there is no need to switch the control mode.

If there is no state change even by the control of the control unit 260 and it is impossible to control based on the tension information and the image information, the mode switching determining unit 220 sends feedback to a user.

A mode switching unit 230 receives the first and second switching condition control mode switching signals, the third forced switching condition control mode switching signal, and the tension state change control mode switching signal from the mode switching determining unit 220. The mode switching unit 230 controls to switch the control mode from the tension information-based flexible tube control to the image information-based flexible tube control or from the image information-based flexible tube control to the tension information-based flexible tube control according to the control mode switching signals of the mode switching determining unit 220.

The above descriptions substitute for descriptions of a learning unit 240 and a compensation control unit 250.

As illustrated in FIG. 7, the tension information-based flexible tube control is first performed (S21). In a case in which it is determined not to correspond to the predefined tension control modeling (first switching condition) while performing the tension information-based flexible tube control (S22), it is controlled to change the control mode into the image information-based flexible tube control (S23 and S24).

Meanwhile, while controlling from the tension information-based flexible tube control to the image information-based flexible tube control, in a case in which the first switching condition is removed (second switching condition) or the first switching condition is not removed and it is impossible to read the image of the surgical instrument so that the image information-based flexible tube control cannot be maintained anymore, the control is performed as follows.

First, in a case in which the first switching condition is removed (second switching condition) and the tension measurement value is larger than a predetermined threshold value, for instance, the threshold value is 'zero', (second switching condition), the control mode is switched from the image information-based flexible tube control to the tension information-based flexible tube control (S31, S32, S33, and S34).

Meanwhile, in a case in which the first switching condition is not removed and it is impossible to read the image of the surgical instrument (S51), control is performed by the following three methods.

First, as the first method, it is determined whether to conform to the forced control mode switching condition (third forced switching condition), and if it conforms to the forced control mode switching condition, the control mode is unconditionally switched from the image information-based flexible tube control to the tension information-based flexible tube control (S41 and S54*a*).

As the second method, the wire is controlled such that the first switching condition is released by repeatedly controlling the wire so as to be pulled or released (S52*a*). In a case in which the tension measurement value of the wire is input normally according to control of the wire (fourth switching condition), the control mode is unconditionally switched from the image information-based flexible tube control to the tension information-based flexible tube control (S53*a* and S54*a*). In a case in which the tension measurement value is not input normally not to satisfy the fourth switching condition, the second method is changed to the following third method or feedback is sent to the user finally.

As the third method, the position of the surgical instrument or the surgical instrument image capturing unit 211 is controlled so that the image of the surgical instrument is readable (S52*b*). In a case in which it is determined that it is possible to read the image according to the control of location (fourth switching condition), the image information-based flexible tube control is maintained (S53*b* and S54*b*). If it is impossible to read the image not to satisfy the fourth switching condition, the third method is changed to the above-mentioned second method or feedback is sent to the user finally.

(Configuration and Function of Hysteresis Compensation Control Apparatus: Third Embodiment)

Figure 8:
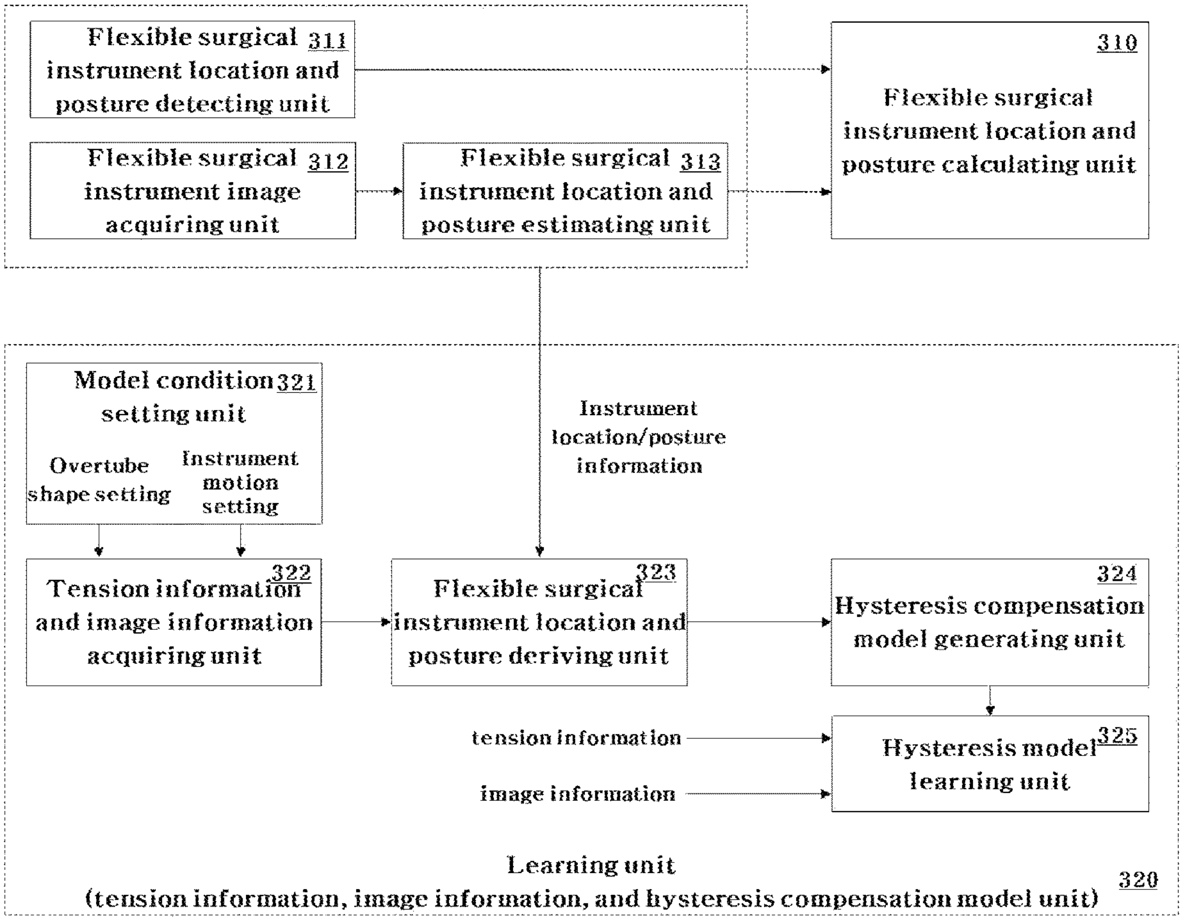
FIG. 8 is a schematic diagram of a configuration for learning a hysteresis compensation model according to a third embodiment of the present invention.
Figure 9:
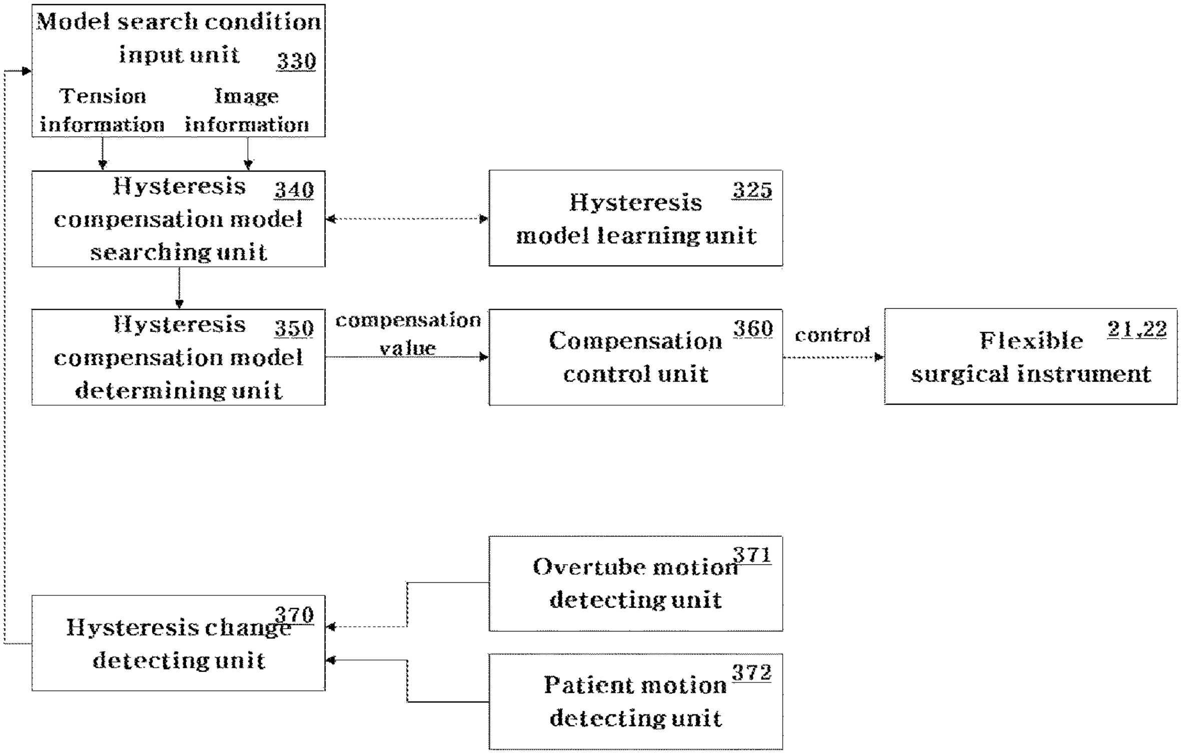
FIG. 9 is a schematic diagram of a configuration for a hysteresis compensation control according to the third embodiment of the present invention.

In general, hysteresis is varied according to the level of friction between a wire and a sheath, and the shape of the sheath is also varied according to the shape of an overtube. Therefore, friction between the wire and the sheath is changed. So, characteristics of the hysteresis are changed, and so, the position and posture (bending angle) of the flexible surgical instrument are changed according to the shape of the overtube even if there is driving force of the same wires. Therefore, the hysteresis compensation control apparatus for the flexible overtube according to the third embodiment of the present invention is an apparatus to search a hysteresis characteristics model suitable for the change in shape of the overtube and changes in location and posture of the flexible surgical instrument to derive a compensation value. Referring to FIGS. 8 and 9, the hysteresis compensation control apparatus for the flexible overtube according to the third embodiment of the present invention will be described in detail.

First, the hysteresis compensation model is learned and corrected through learning of the hysteresis model, the corrected hysteresis compensation model is searched according to model searching conditions to determine a hysteresis compensation model. A compensation value is derived by the determined compensation model, thereby compensating and controlling the flexible surgical instruments 21 and 22.

First, referring to FIG. 8, learning of the hysteresis model will be described. As illustrated in FIG. 8, a flexible surgical instrument location and posture calculating unit 310 calculates location and posture values of the flexible surgical instruments 21 and 22 driven by traction of the wire while being inserted into the channel of the overtube. The location and posture value of the flexible surgical instrument may be calculated by the following two methods.

In the first method, a flexible surgical instrument location and posture detecting unit 311 detects and calculates an actual location and posture value of the flexible surgical instrument through sensors. So, various sensors are arranged. As an example of the sensors, there are FBG sensors (optical fiber grating elements), magnetic sensors, or cameras. The actual location and posture value of the flexible surgical instrument may be a bending angle of the flexible surgical instrument or a measurement value according to forward and backward movement or rotation of the flexible surgical instrument. The tension information may be a tension value or a pulled amount of the wire measured with an encoder.

In the second method, a flexible surgical instrument image acquiring unit 312 acquires an image of the flexible surgical instrument. The acquired image of the flexible surgical instrument is stored as a data set. A flexible surgical instrument location and posture estimating unit 313 matches a location and posture value of the flexible surgical instrument with an image data set of the input flexible surgical instrument and stores it as a data set. Therefore, the flexible surgical instrument location and posture estimating unit 313 can estimate an actual location and posture value of the flexible surgical instrument matched based on the image data set transmitted from the flexible surgical instrument image acquiring unit 312. The image information of the flexible surgical instrument is the image data set displayed on a camera 111 inserted into a channel of an overtube.

A model condition setting unit 321 sets to control a shape of the overtube into a predetermined shape or to control a motion of the flexible surgical instrument into a predetermined motion in order to set a hysteresis compensation model condition. As an example, the overtube can be changed into various shapes, and also the motion of the flexible surgical instrument can be varied according to surgical operations. Therefore, the model condition setting unit 321 sets various possible environment variables (shape of the overtube and motion of the flexible surgical instrument), and generates a hysteresis compensation model according to the environment variable setting.

A tension information and image information acquiring unit 322 acquires tension information and image information according to hysteresis compensation model conditions set by the model condition setting unit 321 in various ways. Additionally, the tension information and image information acquiring unit 322 stores an input data set (input information) for inputting the acquired tension information and image information into a hysteresis compensation model generating unit. The tension information can be measured through the tension measuring unit 112, and the image information can be acquired through the flexible surgical instrument image acquiring unit 312 or the surgical instrument image capturing unit 111.

A flexible surgical instrument location and posture deriving unit 323 derives location and posture values of the flexible surgical instrument when the tension information and image information acquiring unit 322 obtains input information. As described above, the location and posture value of the flexible surgical instrument can be derived from the sensor or the image data set. Additionally, the flexible surgical instrument location and posture deriving unit 323 stores the derived location and posture value of the flexible surgical instrument as an output data set (output information).

A hysteresis compensation model generating unit 324 receives tension information and image information of the wire, which are the input data set obtained according to the shape control of the overtube and the motion control of the flexible surgical instrument set by the model condition setting unit 321, and the location and posture value of the flexible surgical instrument, which is the output data set when the input information is obtained. The hysteresis compensation model generating unit 324 receives the input data set and the output data set to generate hysteresis compensation models according to various environment variables set by the model condition setting unit 321, namely, according to a change in shape of the overtube and a change in motion of the flexible surgical instrument.

A hysteresis model learning unit 325 learns the tension information, the image information, and the hysteresis compensation model generated by the hysteresis compensation generating unit 324 to calibrate the hysteresis compensation model.

As described above, after learning and calibrating the hysteresis compensation model through the hysteresis model learning, the hysteresis model learning unit 325 searches the calibrated hysteresis compensation model according to model search conditions to determine a hysteresis compensation model, and derives a compensation value by the determined compensation model to compensate and control the flexible surgical instruments 21 and 22. Hereinafter, referring to FIG. 9, the hysteresis compensation control apparatus according to the third embodiment of the present invention will be described.

A model search condition input unit 330 obtains tension information and image information caused by a specific motion of the flexible surgical instrument after the overtube reaches a target position having a lesion. As described above, the tension information can be measured by the tension measuring unit 112, and the image information can be obtained through the flexible surgical instrument image obtaining unit 312 or the surgical instrument image capturing unit 111. The obtained tension information and image information is transmitted to a hysteresis compensation model searching unit 340.

The hysteresis compensation model searching unit 340 searches the calibrated hysteresis compensation model of the hysteresis model learning unit 325 based on the tension information and the image information input by the model search condition input unit 330.

A hysteresis compensation model determining unit 350 determines the calibrated hysteresis compensation model searched by the hysteresis compensation model searching unit 340, and calculates a compensation value, which is a tension error value, by the determined hysteresis compensation model.

A compensation control unit 360 compensates and controls the flexible tube having the hysteresis characteristics on the basis of the tension error value of the hysteresis compensation model determined by the hysteresis compensation model determining unit 350.

A hysteresis change detecting unit 370 detects motions of the overtube or motions of a patient. The motions of the overtube or the patient correspond to the hysteresis change conditions. In a case in which there is a hysteresis change, it may be necessary to re-search the determined hysteresis compensation model. Therefore, the hysteresis change detecting unit 370 transmits a detection signal to the model search condition input unit 330 when detecting the hysteresis change condition. The model search condition input unit 330 receiving the hysteresis change detection signal re-obtains tension information and image information to re-search the hysteresis compensation model.

The motion of the overtube may be detected, for instance, in a case in which the image is changed without a control input to control the overtube or the flexible surgical instrument, or in a case in which a master manipulation signal to control the overtube is input.

Meanwhile, if the patient moves, the shape of the overtube inserted into the patient's body may be changed. Therefore, the hysteresis change detecting unit 370 predicts the hysteresis change by detecting motions of the patient. The hysteresis change detecting unit 370 can detect the patient's motion by checking the patient's breathing or through changes in images of the patient.

It will be apparent to those skilled in the art that obvious matters in description of the present invention will be omitted, and descriptions of the omitted components (methods) and functions may be fully referenced within the scope of the present invention without departing from the spirit and scope of the present invention. In addition, the above-described components of the present invention have been described for the convenience of description of the present invention, and components that are not described herein may be added within the scope of the present invention without departing from the spirit and scope of the present invention.

For convenience of description, the above-described configuration and function of the respective components have been described separately, but as necessary, any one configuration and function may be incorporated into other components, or may be further subdivided.

Although the present invention has been described with reference to one embodiment of the present invention, the present invention is not limited thereto, and various modifications and applications are possible. That is, it will be appreciated to those skilled in the art that many variations are possible within the scope of the present invention. In addition, it should be noted that detailed descriptions of the known functions and components related to the present invention and the combination relationship for the configuration may be omitted to avoid unnecessarily obscuring the presented embodiments.

What is claimed is:

1. A hysteresis compensation control method, comprising:

receiving both image information and tension information of a flexible surgical instrument driven by a traction wire, wherein both the image information and the tension information are used for mode switching of the flexible surgical instrument driven by the traction wire;

determining a first determination result of whether a current state of the flexible surgical instrument indicating that a tip region image of the flexible surgical instrument is not visible or is hidden by another flexible surgical instrument based on the image information of the flexible surgical instrument;

determining a second determination result of whether the current state of the flexible surgical instrument indicating that the flexible surgical instrument does not correspond to a predefined tension control modeling based on the tension information of the flexible surgical instrument;

generating a control mode switching signal for switching between an image information-based flexible tube control for controlling the flexible surgical instrument based on the image information and a tension information-based flexible tube control for controlling the flexible surgical instrument based on the tension information when the first determination result indicates that the tip region image of the flexible surgical instrument is not visible or is hidden by another flexible surgical instrument based on the image information of the flexible surgical instrument according to the control mode switching signal, switching a first control mode from the image information-based flexible tube control to the tension information-based flexible tube control according to the control mode switching signal;

after the control mode is switched from the image information-based flexible tube control to the tension information-based flexible tube control, determining the second determination result of whether the current state indicating that the flexible surgical instrument does not correspond to the predefined tension control modeling based on the tension information of the flexible surgical instrument, wherein the predefined tension control modeling is determined to be non-corresponding when a load change of the surgical instrument is detected or a tension measurement value of the traction wire is zero, when the second determination result indicates that the current tension state of the flexible surgical instrument does not to correspond to the predefined tension control modeling, switching a second control mode from the tension information-based flexible tube control to the image information-based flexible tube control according to the control mode switching signal; and controlling the flexible surgical instrument having hysteresis characteristics based on a tension error value of the traction wire calculated by a learning model.

2. The hysteresis compensation control method according to claim 1, further comprising:

capturing an image of the flexible surgical instrument using a camera inserted into a channel of a overtube body;

measuring a traction force of the traction wire of the flexible surgical instrument using a tension measuring sensor;

calculating a tension variation that a wire tension value of the traction wire is varied on the basis of the traction force measured by the tension measuring sensor; and comparing and determining the wire tension value input on the basis of the traction force measured by the tension measuring sensor.

3. The hysteresis compensation control method according to claim 1, further comprising:

learning according to a predetermined learning model based on the image information of the flexible surgical instrument and calculating an image error value by learning; and learning according to the predetermined learning model based on the tension information of the flexible surgical instrument and calculating the tension error value by learning.

4. The hysteresis compensation control method according to claim 1, further comprising: switching the image information-based flexible tube control to the tension information-based flexible tube control according to the control mode switching signal.

5. The hysteresis compensation control method according to claim 4, wherein the image information for determining the current state of the flexible surgical instrument is the image information obtained by capturing the tip region of the flexible surgical instrument inserted into a channel of a tube body and towed by the traction wire.

6. The hysteresis compensation control method according to claim 5, further comprising:

capturing an image of the flexible surgical instrument using a camera inserted into a channel of a overtube body; and measuring a traction force of the traction wire of the flexible surgical instrument using a tension measuring sensor, wherein the image information of the tip region of the flexible surgical instrument captured by the camera is used to determine the current state of the flexible surgical instrument.

7. The hysteresis compensation control method according to claim 6, further comprising determining whether it is possible to perform the image information-based flexible tube control on the basis of the image information of the tip region of the flexible surgical instrument.

* * * * *